United States Patent [19]

Szajáni et al.

[11] Patent Number: 5,275,952
[45] Date of Patent: Jan. 4, 1994

[54] ANAYTICAL METHOD FOR THE SELECTIVE DETERMINATION OF SIALIC GLYCOLIPID COMPLEXES

[75] Inventors: Béla Szajáni; Anna Gesztesi née Koszegi; Ferenc Pribék; Béla Schumann; Jolán Babarczi; Edit Kinczel; Irén Milován; Edit Siklósi née Patay; Katalin Ivony née Kladiva, all of Budapest, Hungary

[73] Assignee: Reanal Finomveygszergyar, Budapest, Hungary

[21] Appl. No.: 689,286

[22] PCT Filed: May 12, 1989

[86] PCT No.: PCT/HU89/00021
§ 371 Date: Jun. 3, 1991
§ 102(e) Date: Jun. 3, 1991

[87] PCT Pub. No.: WO90/08317
PCT Pub. Date: Jul. 26, 1990

[30] Foreign Application Priority Data

Jan. 23, 1989 [HU] Hungary ............... 249/89
May 8, 1989 [HU] Hungary ............... 2190/89

[51] Int. Cl.$^5$ .............................. G01N 33/92
[52] U.S. Cl. ............................ 436/64; 436/71; 436/813; 436/95; 436/63
[58] Field of Search ............. 436/63, 64, 93, 94, 436/95, 71, 813, 175, 13, 87

[56] References Cited

U.S. PATENT DOCUMENTS

| | | | |
|---|---|---|---|
| 4,115,062 | 9/1978 | Morre et al. | 436/71 |
| 4,486,531 | 12/1984 | Ziegenhorn et al. | 436/13 |
| 4,520,111 | 5/1985 | Miller | 436/71 |
| 4,746,605 | 5/1988 | Kerscher et al. | 436/175 |
| 4,748,128 | 5/1988 | Katopodis | 436/71 |
| 4,923,439 | 5/1990 | Seidel et al. | 436/71 |

*Primary Examiner*—James C. Housel
*Assistant Examiner*—Lien Tran
*Attorney, Agent, or Firm*—Herbert Dubno; Jonathan Myers

[57] ABSTRACT

A method for the selective determination of sialic acid-carrying glycolipid complexes in blood, in which the serum is diluted with water, then extracted with a water-immiscible organic solvent or solvent mixture to remove neutral lipids, a lipoprotein fraction containing sialic acid-carrying glycolipids is precipitated from the aqueous phase, the precipitated fraction is redissolved, and the sialic acid content of the solution or the amount and quality of the sialic acid-carrying glycolipid are determined by a method known per se. A water-soluble salt of a monovalent, bivalent or trivalent metal other than alkali metal is used as a precipitating agent in an amount corresponding to a final metal ion concentration of 0.005–0.1 mole/l in the mixture, and precipitation is performed at a pH of 1.5 to 8.0.

14 Claims, No Drawings

ANALYTICAL METHOD FOR THE SELECTIVE DETERMINATION OF SIALIC GLYCOLIPID COMPLEXES CROSS REFERENCE TO RELATED APPLICATIONS

This application is a national phase of PCT/HU89/00021 filed May 12, 1989 and based, in turn, on Hungarian national application 249/89 of Jan. 23, 1989 and 2190/89 of May 5, 1989 under the International Convention.

FIELD OF THE INVENTION

The invention relates to an analytical method for the selective determination of sialic acid-carrying glycolipid complexes.

BACKGROUND OF THE INVENTION

Sialic acid (N-acetyl neuraminic acid) appears in the living organism in free and bound states (Advances in Cancer Res. 38, 289–350; 1983). Sialic acid can be bound as a terminal group via an oligosaccharide chain to membrane-bound sphingolipids (J. of Supramolecular Structure 9, 157–177; 1978). The terminology of gangliosides, including glycosphingolipids, is not always unambiguous in the literature. According to Svennerholm (Comprehensive Biochemistry 18, 201; Elsevier, Amsterdam, 1970) these compounds can be classified into the groups of monosialogangliosides, disialogangliosides and trisialogangliosides. The hydrophobic part of the ganglioside is ceramide, which is bound to the membrane with a long unsaturated fatty acid chain. Ceramide is bound to oligosaccharides, i.e. to glucose, galactose, N-acetyl galactosamine and sialic acid, through an amino group.

Owing to the presence of sialic acid bound thereto, the glycosphingolipid macromolecule has a negative charge, and this negative charge influences certain intercellular interactions. Due to the disturbances in biochemical equilibrium in tumorous organisms the intercellular interactions change whereupon the amount of glycolipid-bound sialic acid increases in the blood.

Based on this theoretical recognition several methods have been developed to determine the glycolipid-bound sialic acid content of blood. According to the method of Svennerholm (Biochem. Biophys. Acta 24, 604–611 1957) blood plasma is extracted with a 2:1 mixture of chloroform and methanol to separate glycosphingolipids from the other lipid fractions of blood, and the sialic acid content of glycosphingolipids is measured by a colorimetric reaction produced with resorcinol in the presence of a copper(II) salt. According to Katopodis (U.S. Pat. No. 4,342,567) the glycosphingolipid fraction is precipitated first from the methanolic supernatant with phosphotungstic acid, and the redissolved precipitate is utilized in the colorimetric determination. In this way the specifity of the Svennerholm method could be improved. Sialic acid can also be determined, however, by enzymatic reactions. According to the method disclosed in Clin. Chim. Acta 108, 493–498 (1980) the glycoprotein is split with neuraminidase enzyme and the liberated sialic acid is contacted with N-acetyl-neuraminic acid-aldolase enzyme to obtain pyruvate and N-acetyl-D-mannosamine. The resulting pyruvate is oxidized with pyruvate oxidase into a peroxide which is converted into a colored substance with p-chlorophenol and 4-amino-antipyrine in the presence of peroxidase, and the amount of the resulting coloured substance is determined at 505 nm.

All of the above methods have the common disadvantage that the error of determination exceeds 20%. Since according to the authors there is a rather small difference between normal and pathologic sialic acid levels (values below 18 mg % can be regarded as normal, whereas those exceeding 20 mg % are pathologic), the results may refer to the existence of a malignant disease but cannot be applied as an unambiguous proof of the existence of tumorous or tumour-free state. It is a further disadvantage that certain benign diseases, such as arthritis, psoriasis, ulcer, inflammations and gynecological disorders, may also result in an increase of the sialic acid content of blood (J. Clin. Chem. Biochem. 22, 647–651 1984). Consequently, the method developed so far for the determination of sialic acid content of blood may only give rise to a suspicion of cancer but cannot form a basis for setting up a more accurate diagnosis.

OBJECT OF THE INVENTION

It is the object of our invention to provide an analytical method which may lead to a more reliable diagnosis, enables one to recognize the existence of a tumor state at a very early stage, gives reliable information on distinguishing tumorous and tumor-free states from one another and enables localization of the tumor.

DESCRIPTION OF THE INVENTION

The invention is based on the recognition that, at an appropriate pH and ionic strength, different metal salts are able to separate well-defined subfractions from the complicated composite of glycolipid complexes present in blood. In cancerous processes of different origin or in nontumorous diseases sialic acid binds preferentially to different glycolipid fractions; thus, by measuring the sialic acid content of the separated glycolipid subfraction or by determining the nature of the glycolipid to which sialic acid is bound conclusions can be drawn as to whether an increase in sialic acid level can be attributed to a tumorous process or to a benign disease (such as inflammation, arthritis, a gynecological disorder, etc.), and in tumorous processes conclusion can be drawn on the probable localization of the tumor or on the existence of metastasis. It has also been observed that when utilizing certain metal salts, primarily cadmium salts, as precipitating agent one can recognize a tumorous state at a much earlier stage than is possible using phosphotungstic acid as precipitating agent.

Based on the above, the invention relates to a method for the selective determination of sialic acid-carrying glycolipid complexes in blood, primarily in human blood, in which the serum is diluted with water, then extracted with a water-immiscible organic solvent or solvent mixture to remove neutral lipids, a lipoprotein fraction containing sialic acid-carrying glycolipids is precipitated from the aqueous phase, the precipitated fraction is redissolved, and the sialic acid content of the solution or the amount and quality of the sialic acid-carrying glycolipid are determined by a method known per se. According to the invention a water-soluble salt of a monovalent, bivalent or trivalent metal other than alkali metal is used as the precipitating agent in an amount corresponding to a final metal ion concentration of 0.005–0.1 mole/l in the mixture, and precipitation is performed at a pH of 1.5 to 8.0.

It is preferred to apply the method described in U.S. Pat. No. 4,342,567 to remove the neutral lipids from the serum diluted with water, according to which a 2:1 v/v mixture of chloroform and methanol is utilized as extracting agent. The aqueous methanolic supernatant (in the following: the methanolic supernatant) is processed further in the precipitation step, whereas the lower phase which is a chloroform solution of neutral lipids is discarded.

Thereafter the precipitating agent is added to the aqueous methanolic phase or to an aliquot thereof in an amount to obtain a mixture containing 0.005–0.1 mole/l of metal ion. The precipitating agent is utilized preferably as an aqueous solution. For some metal ions the preferred pH values of precipitation are listed in the table below.

| Metal ion | pH |
|---|---|
| $Fe^{2+}$ | 3.0–3.5 |
| $Fe^{3+}$ | 3.0–5.0 |
| $Co^{2+}$ | 4.0–5.5 |
| $Ni^{2+}$ | 4.5–5.5 |
| $Cd^{2+}$ | 4.5–6.0 |
| $Zn^{2+}$ | 1.5–5.0 |
| $Ag^{+}$ | 6.0–8.0 |
| $Hg^{2+}$ | 1.5–3.0 |
| $Cu^{2+}$ | 3.0–4.5 |
| $Ca^{2+}$ | 4.5–5.5 |
| $Mg^{2+}$ | 5.5–7.0 |

The resulting precipitate is separated and then a) the sialic acid content of the precipitate is determined by a known method, such as on the basis of the colour reaction produced with a mineral acid, a copper-(II) salt and resorcinol as described in U.S. Pat. No. 4,342,567, or by the enzymatic method disclosed in Clin. Chim. Acta 108, 493–498 (1980), or b) the type and amount of glycolipids bound to sialic acid are determined by a known method, such as by high pressure liquid chromatography as described in Clin. Chem. 22, 1516–1521 (1976).

The differential diagnostic value of the method according to the invention can be increased considerably when the sialic acid content of a blood sample of one and the same origin is determined in a series utilizing at least five different metal ions, and the $$\frac{\text{measured value}}{\text{normal value}}$$

ratios (where the term "normal value" refers to the statistically calculated non-pathologic sialic acid concentration utilizing the given metal ion as precipitating agent) are added up. According to our experiences the value of $$\Sigma \frac{\text{measured}}{\text{normal}}$$

decreases for localized tumors in the following order: mammary tumor-colon tumor-ovarian tumor-head/-neck tumor-adenocarcinoma-non-tumorous disease-healthy tumor-free state.

Similarly, a differential diagnostic series can be obtained when the results of the sialic acid determination according to the invention, performed with at least five different metal ions, are divided with the result of a known sialic acid determination (e.g. with the result of the determination disclosed in U.S. Pat. No. 4,342,567 in which a sialic acid content independent of the origin of sialic acid is measured), and these quotients are added up. The individual quotients may also have differential diagnostic value.

SPECIFIC EXAMPLES

The invention is elucidated in detail by the aid of the following non-limiting examples. In the examples the blood samples were pre-treated and the sialic acid content of the precipitate was measured as follows:

Venal blood was used for the determination. After blood sampling the sample was centrifuged for 15 minutes at 4000 r.p.m., and 0.6 ml of the sample was frozen. The lipid-bound sialic acid concentration of the sample stored at $-20°$ C. remains unchanged for 6 months.

Prior to starting the analysis the test tubes were thoroughly rinsed with methanol, dried, and pre-cooled in a refrigerator. 0.2 ml of the serum sample and 0.2 ml of bidistilled water were filled into each of the test tubes, the mixture was stirred with a Vortex stirrer for 15 seconds and then placed into ice water bath (0° C.). Two parallel samples, each, were prepared from each of the sera to be examined and from the controls.

3 ml, each, of a pre-cooled 2:1 v/v mixture of chloroform and methanol were filled into all of the test tubes, and the contents of the test tubes were stirred with a Vortex stirrer for 30 seconds. Then the test tubes were placed again into the ice water bath. 0.5 ml, each, of bidistilled water pre-cooled to $+4°$ C. was added to the individual samples, the contents of the test tubes were stirred with a Vortex stirrer for 15 seconds, and then the mixtures were allowed to stand at room temperature for 5 minutes. Thereafter the samples were centrifuged for 10 minutes at 3000 r.p.m. 1 ml, each, of the supernatant was filled cautiously into numbered centrifuge tubes, the aqueous metal salt solution of the amount and concentration given in the examples was added, the pH of the mixture was adjusted to the value given in the examples, the contents of the individual centrifuge tubes were stirred with a Vortex stirrer, and then allowed to stand for 5 minutes.

At the end of the standing period the contents of the individual centrifuge tubes were centrifuged for 15 minutes at 4000 r.p.m., and then the supernatant was separated completely from the precipitate by decanting (the supernatant was discarded).

1 ml, each, of a tris buffer solution was introduced into the individual centrifuge tubes, redissolving thereby the precipitate. Tris buffer solution was prepared by dissolving 10 mmoles of tris(hydroxymethyl) aminomethane in one liter of bidistilled water and adjusting the pH of the resulting solution to 8.6.

Standard and blank samples were prepared for the photometric measurements as follows:

50 mg of analytically pure sialic acid were dissolved in 100 ml of bidistilled water, and the resulting solution was utilized as stock solution to prepare two further dilutions (25 mg/100 ml and 12.5 mg/100 ml in concentration) with bidistilled water. The standard solutions were stored at $+4°$ C. Samples of 0.2 ml, each, of the standard solutions with three different concentrations were filled into centrifuge tubes, and the volume of the solution was adjusted to 1 ml with bidistilled water in each of the centrifuge tubes. 1 ml of bidistilled water was used as a blank.

1 ml, each, of resorcinol reagent solution was added to all of the samples (standard, blank, control, test serum). The resorcinol reagent solution was prepared as follows: 2 g of analytically pure resorcinol were dissolved in 100 ml of bidistilled water. 2.49 g of anhydrous copper(II) sulfate were dissolved in 100 ml of bidistilled water. Thereafter 10 ml of the resorcin solution were admixed with 0.25 ml of the copper(II) sulfate solution and 9.75 ml of bidistilled water, and 100 ml of analytically pure concentrated aqueous hydrochloric acid were added to the mixture.

The test tubes were placed into a 100° C. water bath for exactly 10 minutes. Therafter all of the test tubes were immediately immersed into a 0° C. ice water bath and were kept there for 10 minutes. 2 ml, each, of a 85:15 v/v mixture of butyl acetate and n-butanol were introduced into the individual test tubes and the contents of the test tubes were stirred with a Vortex stirrer for 5 minutes. The mixtures were allowed to stand with occasional stirring, the samples were centrifuged for 10 minutes at 2500 r.p.m., and then the blue supernatants were filled from each centrifuge tube into a measuring cell. The density of the blue color formed does not change over 6 hours.

Photometric measurement was performed at a wavelength of 580 nm. The zero point of the photometer was adjusted for bidistilled water. Thereafter, depending on the type of the photometer used (single-beam or double-beam), the measurement was performed either against the blank, or the extinction of the blank was substracted from the measured extinction of the sample to obtain a corrected value:

$$E(corr) = E(measured) - E(blank)$$

Sialic acid content was calculated by one of the following two methods:

1) From the results obtained with standard sialic acid samples of known sialic acid concentrations, extinction vs. concentration curves were constructed either graphically or by calculation. Due to the dilution steps, the original concentrations should be recalculated according to the following table:

| Original concentration (mg/100 ml) | Meausured concentration ($\mu$g/200 ml) | Extinction |
|---|---|---|
| 50 | 100 | 0.508 |
| 25 | 50 | 0.252 |
| 12.5 | 25 | 0.127 |

From the calibration curve constructed as described above the sialic acid content (A) of the supernatant sample, 1 ml in volume, can be determined. The curve gives the sialic acid content in units of $\mu$g of sialic acid/1 ml of supernatant. The sialic acid content of the blood serum can be calculated from the formula $$\text{Sialic acid content(mg/100 ml)} = A \times 0.72,$$

where A is the sialic acid content of the supernatant in units of $\mu$g/ml and 0.72 is a factor which comprises the degree of dilution and the conversion of $\mu$g to mg.

2) According to the second method of calculation reference serum samples with known sialic acid concentrations were applied. From several parallel measurements a factor F was calculated according to the formula $$F = C(ref)/E(ref),$$

where C(ref) is the sialic acid content of the reference serum in mg/100 ml and E(ref) is the extinction of the reference serum. The sialic acid content of the sample to be tested can be calculated from the formula $$\text{Sialic acid content(mg/100 ml)} = E(m) \times F,$$

where E(m) is the measured extinction of the sample to be tested.

EXAMPLE 1

Serum originating from a healthy person was extracted with a mixture of chloroform and methanol as described above. The methanolic supernatant was admixed in a ratio of 10:1 with a 0.5 mole/liter solution of $NiCl_2$ at a pH of 5.5 to form a precipitate, and the sialic acid content of the precipitate was measured. A value of 4.65 mg % was obtained.

EXAMPLE 2

Serum originating from a healthy person was extracted with a mixture of chloroform and methanol as described above. The methanolic supernatant was admixed in a ratio of 10:1 with a 1.0 mole/liter solution of $NiCl_2$ at a pH of 5.3 to form a precipitate, and the sialic acid content of the precipitate was measured. A value of 6.43 mg % was obtained.

EXAMPLE 3

Serum originating from a healthy person was extracted with a mixture of chloroform and methanol as described above. The methanolic supernatant was admixed in a ratio of 10:1 with a 0.1 mole/liter solution of $CdCl_2$ at a pH of 5.9 to form a precipitate, and the sialic acid content of the precipitate was measured. A value of 11.52 mg % was obtained.

EXAMPLE 4

Serum originating from a healthy person was extracted with a mixture of chloroform and methanol as described above. The methanolic supernatant was admixed in a ratio of 10:1 with a 0.5 mole/liter solution of $CdCl_2$ at a pH of 5.5 to form a precipitate, and the sialic acid content of the precipitate was measured. A value of 10.48 mg % was obtained.

EXAMPLE 5

Serum originating from a healthy person was extracted with a mixture of chloroform and methanol as described above. The methanolic supernatant was admixed in a ratio of 10:1 with a 1.0 mole/liter solution of $CdCl_2$ at a pH of 5.3 to form a precipitate, and the sialic acid content of the precipitate was measured. A value of 14.81 mg % was obtained.

EXAMPLE 6

Serum originating from a healthy person was extracted with a mixture of chloroform and methanol as described above. The methanolic supernatant was admixed in a ratio of 10:1 with a 0.1 mole/liter solution of $FeSO_4$ at a pH of 3.3 to form a precipitate, and the sialic acid content of the precipitate was measured. A value of 9.08 mg % was obtained.

EXAMPLE 7

Serum originating from a healthy person was extracted with a mixture of chloroform and methanol as described above. The methanolic supernatant was admixed in a ratio of 10:1 with a 0.5 mole/liter solution of $FeSO_4$ at a pH of 3.0 to form a precipitate, and the sialic acid content of the precipitate was measured. A value of 9.54 mg % was obtained.

EXAMPLE 8

Serum originating from a healthy person was extracted with a mixture of chloroform and methanol as described above. The methanolic supernatant was admixed in a ratio of 10:1 with a 1.0 mole/liter solution of $FeSO_4$ at a pH of 2.9 to form a precipitate, and the sialic acid content of the precipitate was measured. A value of 9.52 mg % was obtained.

EXAMPLE 9

Serum originating from a healthy person was extracted with a mixture of chloroform and methanol as described above. The methanolic supernatant was admixed in a ratio of 10:1 with a 0.1 mole/liter solution of $ZnCl_2$ at a pH of 2.7 to form a precipitate, and the sialic acid content of the precipitate was measured. A value of 6.52 mg % was obtained.

EXAMPLE 10

Serum originating from a healthy person was extracted with a mixture of chloroform and methanol as described above. The methanolic supernatant was admixed in a ratio of 10:1 with a 0.5 mole/liter solution of $ZnCl_2$ at a pH of 1.9 to form a precipitate, and the sialic acid content of the precipitate was measured. A value of 12.34 mg % was obtained.

EXAMPLE 11

Serum originating from a healthy person was extracted with a mixture of chloroform and methanol as described above. The methanolic supernatant was admixed in a ratio of 10:1 with a 0.1 mole/liter solution of $Pb(NO_3)_2$ at a pH of 4.4 to form a precipitate, and the sialic acid content of the precipitate was measured. A value of 8.61 mg % was obtained.

EXAMPLE 12

Serum originating from a healthy person was extracted with a mixture of chloroform and methanol as described above. The methanolic supernatant was admixed in a ratio of 10:1 with a 0.5 mole/liter solution of $Pb(NO_3)_2$ at a pH of 3.7 to form a precipitate, and the sialic acid content of the precipitate was measured. A value of 12.11 mg % was obtained.

EXAMPLE 13

Serum originating from a healthy person was extracted with a mixture of chloroform and methanol as described above. The methanolic supernatant was admixed in a ratio of 10:1 with a 1.0 mole/liter solution of $Pb(NO_3)_2$ at a pH of 3.5 to form a precipitate, and the sialic acid content of the precipitate was measured. A value of 12.35 mg % was obtained.

EXAMPLE 14

Serum originating from a healthy person was extracted with a mixture of chloroform and methanol as described above. The methanolic supernatant was admixed in a ratio of 10:1 with a 0.1 mole/liter solution of $AgNO_3$ at a pH of 8.5 to form a precipitate and the sialic acid content of the precipitate was measured. A value of 9.89 mg % was obtained.

EXAMPLE 15

Serum originating from a healthy person was extracted with a mixture of chloroform and methanol as described above. The methanolic supernatant was admixed in a ratio of 10:1 with a 0.5 mole/liter solution of $AgNO_3$ at a pH of 6.0 to form a precipitate, and the sialic acid content of the precipitate was measured. A value of 14.67 mg % was obtained.

EXAMPLE 16

Serum originating from a healthy person was extracted with a mixture of chloroform and methanol as described above. The methanolic supernatant was admixed in a ratio of 10:1 with a 1.0 mole/liter solution of $AgNO_3$ at a pH of 5.8 to form a precipitate, and the sialic acid content of the precipitate was measured. A value of 14.81 mg % was obtained.

EXAMPLE 17

Serum originating from a healthy person was extracted with a mixture of chloroform and methanol as described above. The methanolic supernatant was admixed in a ratio of 10:1 with a 0.1 mole/liter solution of $HgCl_2$ at a pH of 1.9 to form a precipitate, and the sialic acid content of the precipitate was measured. A value of 6.05 mg % was obtained.

EXAMPLE 18

Serum originating from a healthy person was extracted with a mixture of chloroform and methanol as described above. The methanolic supernatant was admixed in a ratio of 10:1 with a 0.5 mole/liter solution of $HgCl_2$ at a pH of 1.7 to form a precipitate, and the sialic acid content of the precipitate was measured. A value of 7.68 mg % was obtained.

EXAMPLE 19

Serum originating from a healthy person was extracted with a mixture of chloroform and methanol as described above. The methanolic supernatant was admixed in a ratio of 10:1 with a 1.0 mole/liter solution of $HgCl_2$ at a pH of 1.5 to form a precipitate, and the sialic acid content of the precipitate was measured. A value of 11.99 mg % was obtained.

EXAMPLE 20

Serum originating from a healthy person was extracted with a mixture of chloroform and methanol as described above. The methanolic supernatant was admixed in a ratio of 10:1 with a 0.1 mole/liter solution of $CuSO_4$ at a pH of 4.2 to form a precipitate, and the sialic acid content of the precipitate was measured. A value of 10.13 mg % was obtained.

EXAMPLE 21

Serum originating from a healthy person was extracted with a mixture of chloroform and methanol as described above. The methanolic supernatant was admixed in a ratio of 10:1 with a 0.5 mole/liter solution of $CuSO_4$ at a pH of 3.8 to form a precipitate, and the sialic acid content of the precipitate was measured. A value of 10.48 mg % was obtained.

EXAMPLE 22

Serum originating from a healthy person was extracted with a mixture of chloroform and methanol as described above. The methanolic supernatant was admixed in a ratio of 10:1 with a 1.0 mole/liter solution of CuSO$_4$ at a pH of 3.6 to form a precipitate, and the sialic acid content of the precipitate was measured. A value of 12.22 mg % was obtained.

EXAMPLE 23

Serum originating from a healthy person was extracted with a mixture of chloroform and methanol as described above. The methanolic supernatant was admixed in a ratio of 10:1 with a 0.1 mole/liter solution of CaCl$_2$ at a pH of 5.5 to form a precipitate, and the sialic acid content of the precipitate was measured. A value of 3.72 mg % was obtained.

EXAMPLE 24

Serum originating from a healthy person was extracted with a mixture of chloroform and methanol as described above. The methanolic supernatant was admixed in a ratio of 10:1 with a 0.5 mole/liter solution of CaCl$_2$ at a pH of 5.4 to form a precipitate, and the sialic acid content of the precipitate was measured. A value of 3.02 mg % was obtained.

EXAMPLE 25

Serum originating from a healthy person was extracted with a mixture of chloroform and methanol as described above. The methanolic supernatant was admixed in a ratio of 10:1 with a 1.0 mole/liter solution of CaCl$_2$ at a pH of 5.3 to form a precipitate, and the sialic acid content of the precipitate was measured. A value of 7.05 mg % was obtained.

EXAMPLE 26

Serum originating from a healthy person was extracted with a mixture of chloroform and methanol as described above. The methanolic supernatant was admixed in a ratio of 10:1 with a 0.1 mole/liter solution of MgCl$_2$ at a pH of 6.1 to form a precipitate, and the sialic acid content of the precipitate was measured. A value of 4.19 mg % was obtained.

EXAMPLE 27

Serum originating from a healthy person was extracted with a mixture of chloroform and methanol as described above. The methanolic supernatant was admixed in a ratio of 10:1 with a 0.5 mole/liter solution of MgCl$_2$ at a pH of 6.7 to form a precipitate, and the sialic acid content of the precipitate was measured. A value of 3.61 mg % was obtained.

EXAMPLE 28

Serum originating from a healthy person was extracted with a mixture of chloroform and methanol as described above. The methanolic supernatant was admixed in a ratio of 10:1 with a 1.0 mole/liter solution of MgCl$_2$ at a pH of 6.5 to form a precipitate, and the sialic acid content of the precipitate was measured. A value of 4.81 mg % was obtained.

EXAMPLE 29

Serum originating from a patient with mammary cancer was extracted with a mixture of chloroform and methanol as described above. The methanolic supernatant was admixed in a ratio of 10:1 with a 1.0 mole/liter solution of NiCl$_2$ at a pH of 5.3 to form a precipitate, and the sialic acid content of the precipitate was measured. A value of 28.87 mg % was obtained.

EXAMPLE 30

Serum originating from a patient with mammary cancer was extracted with a mixture of chloroform and methanol as described above. The methanolic supernatant was admixed in a ratio of 10:1 with a 1.0 mole/liter solution of CdCl$_2$ at a pH of 5.3 to form a precipitate, and the sialic acid content of the precipitate was measured. A value of 41.31 mg % was obtained.

EXAMPLE 31

Serum originating from a patient with mammary cancer was extracted with a mixture of chloroform and methanol as described above. The methanolic supernatant was admixed in a ratio of 10:1 with a 1.0 mole/liter solution of FeSO$_4$ at a pH of 2.9 to form a precipitate, and the sialic acid content of the precipitate was measured. A value of 33.39 mg % was obtained.

EXAMPLE 32

Serum originating from a patient with mammary cancer was extracted with a mixture of chloroform and methanol as described above. The methanolic supernatant was admixed in a ratio of 10:1 with a 1.0 mole/liter solution of ZnCl$_2$ at a pH of 1.7 to form a precipitate, and the sialic acid content of the precipitate was measured. A value of 39.41 mg % was obtained.

EXAMPLE 33

Serum originating from a patient with mammary cancer was extracted with a mixture of chloroform and methanol as described above. The methanolic supernatant was admixed in a ratio of 10:1 with a 1.0 mole/liter solution of ZnSO$_4$ at a pH of 1.7 to form a precipitate, and the sialic acid content of the precipitate was measured. A value of 38.90 mg % was obtained.

EXAMPLE 34

Serum originating from a patient with mammary cancer was extracted with a mixture of chloroform and methanol as described above. The methanolic supernatant was admixed in a ratio of 10:1 with a 1.0 mole/liter solution of Pb(NO$_3$)$_2$ at a pH of 3.5 to form a precipitate, and the sialic acid content of the precipitate was measured. A value of 45.02 mg % was obtained.

EXAMPLE 35

Serum originating from a patient with mammary cancer was extracted with a mixture of chloroform and methanol as described above. The methanolic supernatant was admixed in a ratio of 10:1 with a 1.0 mole/liter solution of AgNO$_3$ at a pH of 5.8 to form a precipitate, and the sialic acid content of the precipitate was measured. A value of 29.58 mg % was obtained.

EXAMPLE 36

Serum originating from a patient with mammary cancer was extracted with a mixture of chloroform and methanol as described above. The methanolic supernatant was admixed in a ratio of 10:1 with a 1.0 mole/liter solution of HgCl$_2$ at a pH of 1.5 to form a precipitate, and the sialic acid content of the precipitate was measured. A value of 33.89 mg % was obtained.

EXAMPLE 37

Serum originating from a patient with mammary cancer was extracted with a mixture of chloroform and methanol as described above. The methanolic supernatant was admixed in a ratio of 10:1 with a 1.0 mole/liter solution of $CuSO_4$ at a pH of 3.6 to form a precipitate, and the sialic acid content of the precipitate was measured. A value of 37.20 mg % was obtained.

EXAMPLE 38

Serum originating from a patient with mammary cancer was extracted with a mixture of chloroform and methanol as described above. The methanolic supernatant was admixed in a ratio of 10:1 with a 1.0 mole/liter solution of $CaCl_2$ at a pH of 5.3 to form a precipitate, and the sialic acid content of the precipitate was measured. A value of 28.18 mg % was obtained.

EXAMPLE 39

Serum originating from a patient with mammary cancer was extracted with a mixture of chloroform and methanol as described above. The methanolic supernatant was admixed in a ratio of 10:1 with a 1.0 mole/liter solution of $MgCl_2$ at a pH of 6.5 to form a precipitate, and the sialic acid content of the precipitate was measured. A value of 25.67 mg % was obtained.

EXAMPLE 40

Serum originating from a patient with ovarian cancer was extracted with a mixture of chloroform and methanol as described above. The methanolic supernatant was admixed in a ratio of 10:1 with a 1.0 mole/liter solution of $NiCl_2$ at a pH of 5.3 to form a precipitate, and the sialic acid content of the precipitate was measured. A value of 22.09 mg % was obtained.

EXAMPLE 41

Serum originating from a patient with ovarian cancer was extracted with a mixture of chloroform and methanol as described above. The methanolic supernatant was admixed in a ratio of 10:1 with a 1.0 mole/liter solution of $CdCl_2$ at a pH of 5.3 to form a precipitate, and the sialic acid content of the precipitate was measured. A value of 25.80 mg % was obtained.

EXAMPLE 42

Serum originating from a patient with ovarian cancer was extracted with a mixture of chloroform and methanol as described above. The methanolic supernatant was admixed in a ratio of 10:1 with a 1.0 mole/liter solution of $FeSO_4$ at a pH of 2.9 to form a precipitate, and the sialic acid content of the precipitate was measured. A value of 18.75 mg % was obtained.

EXAMPLE 43

Serum originating from a patient with ovarian cancer was extracted with a mixture of chloroform and methanol as described above. The methanolic supernatant was admixed in a ratio of 10:1 with a 1.0 mole/liter solution of $ZnCl_2$ at a pH of 1.7 to form a precipitate, and the sialic acid content of the precipitate was measured. A value of 23.77 mg % was obtained.

EXAMPLE 44

Serum originating from a patient with ovarian cancer was extracted with a mixture of chloroform and methanol as described above. The methanolic supernatant was admixed in a ratio of 10:1 with a 1.0 mole/liter solution of $ZnSO_4$ at a pH of 1.7 to form a precipitate, and the sialic acid content of the precipitate was measured. A value of 26.87 mg % was obtained.

EXAMPLE 45

Serum originating from a patient with ovarian cancer was extracted with a mixture of chloroform and methanol as described above. The methanolic supernatant was admixed in a ratio of 10:1 with a 1.0 mole/liter solution of $Pb(NO_3)_2$ at a pH of 3.5 to form a precipitate, and the sialic acid content of the precipitate was measured. A value of 26.63 mg % was obtained.

EXAMPLE 46

Serum originating from a patient with ovarian cancer was extracted with a mixture of chloroform and methanol as described above. The methanolic supernatant was admixed in a ratio of 10:1 with a 1.0 mole/liter solution of $AgNO_3$ at a pH of 5.8 to form a precipitate, and the sialic acid content of the precipitate was measured. A value of 28.66 mg % was obtained.

EXAMPLE 47

Serum originating from a patient with ovarian cancer was extracted with a mixture of chloroform and methanol as described above. The methanolic supernatant was admixed in a ratio of 10:1 with a 1.0 mole/liter solution of $HgCl_2$ at a pH of 1.5 to form a precipitate, and the sialic acid content of the precipitate was measured. A value of 33.08 mg % was obtained.

EXAMPLE 48

Serum originating from a patient with overian cancer was extracted with a mixture of chloroform and methanol as described above. The methanolic supernatant was admixed in a ratio of 10:1 with a 1.0 mole/liter solution of $CuSO_4$ at a pH of 3.6 to form a precipitate, and the sialic acid content of the precipitate was measured. A value of 26.63 mg % was obtained.

EXAMPLE 49

Serum originating from a patient with ovarian cancer was extracted with a mixture of chloroform and methanol as described above. The methanolic supernatant was admixed in a ratio of 10:1 with a 1.0 mole/liter solution of $CaCl_2$ at a pH of 5.3 tc form a precipitate, and the sialic acid content of the precipitate was measured. A value of 13.26 mg % was obtained.

EXAMPLE 50

Serum originating from a patient with ovarian cancer was extracted with a mixture of chloroform and methanol as described above. The methanolic supernatant was admixed in a ratio of 10:1 with a 1.0 mole/liter solution of $MgCl_2$ at a pH of 6.5 to form a precipitate, and the sialic acid content of the precipitate was measured. A value of 11.82 mg % was obtained.

EXAMPLE 51

Serum originating from a patient with head/neck cancer was extracted with a mixture of chloroform and methanol as described above. The methanolic supernatant was admixed in a ratio of 10:1 with a 1.0 mole/liter solution of $NiCl_2$ at a pH of 5.3 to form a precipitate, and the sialic acid content of the precipitate was measured. A value of 12.62 mg % was obtained.

EXAMPLE 52

Serum originating from a patient with head/neck cancer was extracted with a mixture of chloroform and methanol as described above. The methanolic supernatant was admixed in a ratio of 10:1 with a 1.0 mole/liter solution of CdCl$_2$ at a pH of 5.3 to form a precipitate, and the sialic acid content of the precipitate was measured. A value of 21.99 mg % was obtained.

EXAMPLE 53

Serum originating from a patient with head/neck cancer was extracted with a mixture of chloroform and methanol as described above. The methanolic supernatant was admixed in a ratio of 10:1 with a 1.0 mole/liter solution of FeSO$_4$ at a pH of 2.9 to form a precipitate, and the sialic acid content of the precipitate was measured. A value of 16.09 mg % was obtained.

EXAMPLE 54

Serum originating from a patient with head/neck cancer was extracted with a mixture of chloroform and methanol as described above. The methanolic supernatant was admixed in a ratio of 10:1 with a 1.0 mole/liter solution of ZnCl$_2$ at a pH of 1.7 to form a precipitate, and the sialic acid content of the precipitate was measured. A value of 19.56 mg % was obtained.

EXAMPLE 55

Serum originating from a patient with head/neck cancer was extracted with a mixture of chloroform and methanol as described above. The methanolic supernatant was admixed in a ratio of 10:1 with a 1.0 mole/liter solution of ZnSO$_4$ at a pH of 1.7 to form a precipatate, and the sialic acid content of the precipitate was measured. A value of 21.41 mg % was obtained.

EXAMPLE 56

Serum originating from a patient with head/neck cancer was extracted with a mixture of chloroform and methanol as described above. The methanolic supernatant was admixed in a ratio of 10:1 with a 1.0 mole/liter solution of Pb(NO$_3$)$_2$ at a pH of 3.5 to form a precipitate, and the sialic acid content of the precipitate was measured. A value of 29.98 mg % was obtained.

EXAMPLE 57

Serum originating from a patient with head/neck cancer was extracted with a mixture of chloroform and methanol as described above. The methanolic supernatant was admixed in a ratio of 10:1 with a 1.0 mole/liter solution of AgNO$_3$ at a pH of 5.8 to form a precipitate, and the sialic acid content of the precipitate was measured. A value of 14.93 mg % was obtained.

EXAMPLE 58

Serum originating from a patient with head/neck cancer was extracted with a mixture of chloroform and methanol as described above. The methanolic supernatant was admixed in a ratio of 10:1 with a 1.0 mole/liter solution of HgCl$_2$ at a pH of 1.5 to form a precipitate, and the sialic acid content of the precipitate was measured. A value of 18.87 mg % was obtained.

EXAMPLE 59

Serum originating from a patient with head/neck cancer was extracted with a mixture of chloroform and methanol as described above. The methanolic supernatant was admixed in a ratio of 10:1 with a 1.0 mole/liter solution of CuSO$_4$ at a pH of 3.6 to form a precipitate, and the sialic acid content of the precipitate was measured. A value of 14.70 mg % was obtained.

EXAMPLE 60

Serum originating from a patient with head/neck cancer was extracted with a mixture of chloroform and methanol as described above. The methanolic supernatant was admixed in a ratio of 10:1 with a 1.0 mole/liter solution of CaCl$_2$ at a pH of 5.3 to form a precipitate, and the sialic acid content of the precipitate was measured. A value of 9.72 mg % was obtained.

EXAMPLE 61

Serum originating from a patient with head/neck cancer was extracted with a mixture of chloroform and methanol as described above. The methanolic supernatant was admixed in a ratio of 10:1 with a 1.0 mole/liter solution of MgCl$_2$ at a pH of 6.5 to form a precipitate, and the sialic acid content of the precipitate was measured. A value of 12.27 mg % was obtained.

EXAMPLE 62

Serum originating from a patient with adenocarcinoma was extracted with a mixture of chloroform and methanol as described above. The methanolic supernatant was admixed in a ratio of 10:1 with a 1.0 mole/liter solution of NiCl$_2$ at a pH of 5.3 to form a precipitate, and the sialic acid content of the precipitate was measured. A value of 11.77 mg % was obtained.

EXAMPLE 63

Serum originating from a patient with adenocarcinoma was extracted with a mixture of chloroform and methanol as described above. The methanolic supernatant was admixed in a ratio of 10:1 with a 1.0 mole/liter solution of CdCl$_2$ at a pH of 5.3 to form a precipitate, and the sialic acid content of the precipitate was measured. A value of 20.09 mg % was obtained.

EXAMPLE 64

Serum originating from a patient with adenocarcinoma was extracted with a mixture of chloroform and methanol as described above. The methanolic supernatant was admixed in a ratio of 10:1 with a 1.0 mole/liter solution of FeSO$_4$ at a pH of 2.9 to form a precipitate, and the sialic acid content of the precipitate was measured. A value of 16.13 mg % was obtained.

EXAMPLE 65

Serum originating from a patient with adenocarcinoma was extracted with a mixture of chloroform and methanol as described above. The methanolic supernatant was admixed in a ratio of 10:1 with a 1.0 mole/liter solution of ZnCl$_2$ at a pH of 1.7 to form a precipitate, and the sialic acid content of the precipitate was measured. A value of 18.69 mg % was obtained.

EXAMPLE 66

Serum originating from a patient with adenocarcinoma was extracted with a mixture of chloroform and methanol as described above. The methanolic supernatant was admixed in a ratio of 10:1 with a 1.0 mole/liter solution of ZnSO$_4$ at a pH of 1.7 to form a precipitate, and the sialic acid content of the precipitate was measured. A value of 17.15 mg % was obtained.

EXAMPLE 67

Serum originating from a patient with adenocarcinoma was extracted with a mixture of chloroform and methanol as described above. The methanolic supernatant was admixed in a ratio of 10:1 with a 1.0 mole/liter solution of Pb(NO$_3$)$_2$ at a pH of 3.5 to form a precipitate, and the sialic acid content of the precipitate was measured. A value of 22.66 mg % was obtained.

EXAMPLE 68

Serum originating from a patient with adenocarcinoma was extracted with a mixture of chloroform and methanol as described above. The methanolic supernatant was admixed in a ratio of 10:1 with a 1.0 mole/liter solution of AgNO$_3$ at a pH of 5.8 to form a precipitate, and the sialic acid content of the precipitate was measured. A value of 16.51 mg % was obtained.

EXAMPLE 69

Serum originating from a patient with adenocarcinoma was extracted with a mixture of chloroform and methanol as described above. The methanolic supernatant was admixed in a ratio of 10:1 with a 1.0 mole/liter solution of HgCl$_2$ at a pH of 1.5 to form a precipitate, and the sialic acid content of the precipitate was measured. A value of 18.94 mg % was obtained.

EXAMPLE 70

Serum originating from a patient with adenocarcinoma was extracted with a mixture of chloroform and methanol as described above. The methanolic supernatant was admixed in a ratio of 10:1 with a 1.0 mole/liter solution of CuSO$_4$ at a pH of 3.6 to form a precipitate, and the sialic acid content of the precipitate was measured. A value of 17.41 mg % was obtained.

EXAMPLE 71

Serum originating from a patient with adenocarcinoma was extracted with a mixture of chloroform and methanol as described above. The methanolic supernatant was admixed in a ratio of 10:1 with a 1.0 mole/liter solution of CaCl$_2$ at a pH of 5.3 to form a precipitate, and the sialic acid content of the precipitate was measured. A value of 9.73 mg % was obtained.

EXAMPLE 72

Serum originating from a patient with adenocarcinoma was extracted with a mixture of chloroform and methanol as described above. The methanolic supernatant was admixed in a ratio of 10:1 with a 1.0 mole/liter solution of MgCl$_2$ at a pH of 6.5 to form a precipitate, and the sialic acid content of the precipitate was measured. A value of 7.94 mg % was obtained.

EXAMPLE 73

Serum originating from a patient with colon cancer was extracted with a mixture of chloroform and methanol as described above. The methanolic supernatant was admixed in a ratio of 10:1 with a 1.0 mole/liter solution of NiCl$_2$ at a pH of 5.3 to form a precipitate, and the sialic acid content of the precipitate was measured. A value of 20.70 mg % was obtained.

EXAMPLE 74

Serum originating from a patient with colon cancer was extracted with a mixture of chloroform and methanol as described above. The methanolic supernatant was admixed in a ratio of 10:1 with a 1.0 mole/liter solution of CdCl$_2$ at a pH of 5.3 to form a precipitate, and the sialic acid content of the precipitate was measured. A value of 32.14 mg % was obtained.

EXAMPLE 75

Serum originating from a patient with colon cancer was extracted with a mixture of chloroform and methanol as described above. The methanolic supernatant was admixed in a ratio of 10:1 with a 1.0 mole/liter solution of FeSO$_4$ at a pH of 2.9 to form a precipitate, and the sialic acid content of the precipitate was measured. A value of 24.23 mg % was obtained.

EXAMPLE 76

Serum originating from a patient with colon cancer was extracted with a mixture of chloroform and methanol as described above. The methanolic supernatant was admixed in a ratio of 10:1 with a 1.0 mole/liter solution of ZnCl$_2$ at a pH of 1.7 to form a precipitate, and the sialic acid content of the precipitate was measured. A value of 27.52 mg % was obtained.

EXAMPLE 77

Serum originating from a patient with colon cancer was extracted with a mixture of chloroform and methanol as described above. The methanolic supernatant was admixed in a ratio of 10:1 with a 1.0 mole/liter solution of ZnSO$_4$ at a pH of 1.7 to form a precipitate, and the sialic acid content of the precipitate was measured. A value of 3.63 mg % was obtained.

EXAMPLE 78

Serum originating from a patient with colon cancer was extracted with a mixture of chloroform and methanol as described above. The methanolic supernatant was admixed in a ratio of 10:1 with a 1.0 mole/liter solution of Pb(NO$_3$)$_2$ at a pH of 3.5 to form a precipitate, and the sialic acid content of the precipitate was measured. A value of 35.55 mg % was obtained.

EXAMPLE 79

Serum originating from a patient with colon cancer was extracted with a mixture of chloroform and methanol as described above. The methanolic supernatant was admixed in a ratio of 10:1 with a 1.0 mole/liter solution of AgNO$_3$ at a pH of 5.8 to form a precipitate, and the sialic acid content of the precipitate was measured. A value of 29.46 mg % was obtained.

EXAMPLE 80

Serum originating from a patient with colon cancer was extracted with a mixture of chloroform and methanol as described above. The methanolic supernatant was admixed in a ratio of 10:1 with a 1.0 mole/liter solution of HgCl$_2$ at a pH of 1.5 to form a precipitate, and the sialic acid content of the precipitate was measured. A value of 31.66 mg % was obtained.

EXAMPLE 81

Serum originating from a patient with colon cancer was extracted with a mixture of chloroform and methanol as described above. The methanolic supernatant was admixed in a ratio of 10:1 with a 1.0 mole/liter solution of CuSO$_4$ at a pH of 3.6 to form a precipitate, and the sialic acid content of the precipitate was measured. A value of 32.51 mg % was obtained.

EXAMPLE 82

Serum originating from a patient with colon cancer was extracted with a mixture of chloroform and methanol as described above. The methanolic supernatant was admixed in a ratio of 10:1 with a 1.0 mole/liter solution of CaCl$_2$ at a pH of 5.3 to form a precipitate, and the sialic acid content of the precipitate was measured. A value of 18.51 mg % was obtained.

EXAMPLE 83

Serum originating from a patient with colon cancer was extracted with a mixture of chloroform and methanol as described above. The methanolic supernatant was admixed in a ratio of 10:1 with a 1.0 mole/liter solution of MgCl$_2$ at a pH of 6.5 to form a precipitate, and the sialic acid content of the precipitate was measured. A value of 16.68 mg % was obtained.

What we claim is:

1. A method for the selective quantitative determination of a well-defined subfraction of sialic acid-carrying glycolipid complex in blood, in a patient, in order to determine whether said patient is afflicted with a cancer, which comprises the steps of:
   (a) obtaining blood serum from said patient;
   (b) diluting the blood serum with water;
   (c) extracting the diluted blood serum of step (b) with a water-immiscible organic solvent or solvent mixture to remove neutral lipids;
   (d) precipitating from the diluted blood serum, at a pH of 1.5 to 8.0, a subfraction containing a negatively charged sialic acid-carrying glycolipid, using as a sole precipitating agent, a water-soluble salt of a specific monovalent, bivalent, or trivalent metal other than an alkali metal, in an amount corresponding to a final metal ion concentration of 0.005 to 0.1 moles/l to form a mixture of supernatant liquid and precipitate;
   (e) separating the supernatant liquid completely from the precipitate formed in step (d);
   (f) following step (e), redissolving the precipitate of the subfraction containing a sialic acid-carrying glycolipid complex and the specific monovalent, bivalent or trivalent metal other than an alkali metal in a buffer solution and adjusting the pH of the resulting buffered solution to 8.6;
   (g) measuring the amount of sialic acid contained in the glycolipid complex subfraction in the buffered solution prepared according to step (f);
   (h) comparing the amount of measured sialic acid in the sialic acid-carrying glycolipid complex according to step (g) with the amount of sialic acid contained in a standard sialic acid-carrying glycolipid complex obtained from blood sera of a healthy population, also prepared according to steps (a) through (g) using the same monovalent, bivalent, or trivalent metal salt other than an alkail metal salt which was used as precipitating agent; and
   (i) relating any difference in the amount of sialic acid measured in the sample and in the standard to the presence of the specific cancer in said patient.

2. The process defined in claim 1 wherein the cancer with which the patient is afflicted is selected from the group consisting of mammary tumor, colon tumor, ovarian tumor, head or neck tumor and adenocarcinoma.

3. The process defined in claim 1 wherein according to step (f) the buffer solution is a tris buffer solution prepared by dissolving 10 moles of tris(hydroxymethyl)aminomethane in one liter of bidistilled water.

4. A method as claimed in claim 1 wherein a water-soluble Fe$^{2+}$ salt is used as precipitating agent, and precipitation is performed at a pH of 3.0 to 3.5.

5. A method as claimed in claim 1 wherein a water-soluble Fe$^{3+}$ salt is used as precipitating agent, and precipitation is performed at a pH of 3.0 to 5.0.

6. A method as claim in claim 1 wherein a water-soluble Co$^{2+}$ salt is used as precipitating agent, and precipitation is performed at a pH of 4.0 to 5.5.

7. A method as claimed in claim 1 wherein a water-soluble Ni$^{2+}$ salt is used as precipitating agent, and precipitation is performed at a pH of 4.5 to 5.5.

8. A method as claimed in claim 1 wherein a water-soluble Cd$^{2+}$ salt is used as precipitating agent, and precipitation is performed at a pH of 4.5 to 6.0.

9. A method as claimed in claim 1 wherein a water-soluble Zn$^{2+}$ salt is used as precipitating agent, and precipitation is performed at a pH of 1.5 to 5.0.

10. A method as claimed in claim 1 wherein a water-soluble Ag$^{+}$ salt is used as precipitating agent, and precipitation is performed at a pH of 6.0 to 8.0.

11. A method as claimed in claim 1 wherein a water-soluble Hg$^{2+}$ salt is used as precipitating agent, and precipitation is performed at a pH of 1.5 to 3.0.

12. A method as claimed in claim 1 wherein water-soluble Cu$^{2+}$ salt is used as precipitating agent, and precipitation is performed at a pH of 3.0 to 4.5.

13. A method as claimed in claim 1 wherein a water-soluble Ca$^{2+}$ salt is used as precipitating agent, and precipitation is performed at a pH of 4.5 to 5.5.

14. A method as claimed in claim 1 wherein a water-soluble Mg$^{2+}$ salt is used as precipitating agent, and precipitation is performed at a pH of 5.5 to 7.0.

* * * * *